United States Patent
Oren et al.

(10) Patent No.: US 8,282,659 B2
(45) Date of Patent: Oct. 9, 2012

(54) SUTURE MANIPULATING AND CUTTING IMPLEMENT

(75) Inventors: Ran Oren, Doar Na Oshrat (IL); Dan Moor, Doar Na Oshrat (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 223 days.

(21) Appl. No.: 10/591,341

(22) PCT Filed: Mar. 3, 2005

(86) PCT No.: PCT/IL2005/000254
§ 371 (c)(1),
(2), (4) Date: Aug. 31, 2006

(87) PCT Pub. No.: WO2005/084127
PCT Pub. Date: Sep. 15, 2005

(65) Prior Publication Data
US 2007/0173865 A1 Jul. 26, 2007

Related U.S. Application Data

(60) Provisional application No. 60/549,553, filed on Mar. 4, 2004.

(51) Int. Cl.
*A61B 17/04* (2006.01)
(52) U.S. Cl. ........... 606/148; 606/144; 606/139; 289/17
(58) Field of Classification Search .................. 606/148, 606/205, 139, 144; 57/23; 289/17
See application file for complete search history.

(56) References Cited

U.S. PATENT DOCUMENTS

| | | | |
|---|---|---|---|
| 5,176,691 A * | 1/1993 | Pierce | 606/148 |
| 5,292,327 A | 3/1994 | Dodd et al. | |
| 5,324,298 A * | 6/1994 | Phillips et al. | 606/148 |
| 5,395,382 A | 3/1995 | DiGiovanni et al. | |
| 5,397,326 A | 3/1995 | Mangum | |
| 5,423,837 A | 6/1995 | Mericle et al. | |
| 5,609,597 A * | 3/1997 | Lehrer | 606/139 |
| 5,653,719 A | 8/1997 | Raiken | |
| D386,583 S | 11/1997 | Ferragamo et al. | |
| 5,797,929 A * | 8/1998 | Andreas et al. | 606/148 |
| 6,200,329 B1 * | 3/2001 | Fung et al. | 606/232 |
| 6,488,690 B1 | 12/2002 | Morris et al. | |
| 6,511,488 B1 * | 1/2003 | Marshall et al. | 606/148 |

(Continued)

OTHER PUBLICATIONS

IPRP dated Sep. 14, 2006.

(Continued)

*Primary Examiner* — Corrine M. McDermott
*Assistant Examiner* — Mark Mashack

(57) ABSTRACT

An implement for manipulating a knotted suture during a surgical procedure, includes an elongated shaft having a proximal end engageable by the user for manipulating the instrument, and a distal end engageable with the knotted suture to be manipulated. The distal end of the elongated shaft has an end face formed with a recess for receiving the knot of the suture. The distal end of the elongated shaft is formed with an open slot starting from a location spaced from the end face and leading to the recess in the end face, such as to enable the knotted suture to be introduced into the slot and the recess by effecting a sidewise movement. The implement further includes a tubular cutter member enclosing the elongated shaft and formed with an annular cutting edge engageable with a suture in the open slot of the shaft upon movement of the elongated shaft with respect to the tubular cutter member, or by vice-versa.

14 Claims, 2 Drawing Sheets

U.S. PATENT DOCUMENTS

| | | | |
|---|---|---|---|
| 6,716,224 B2 | 4/2004 | Singhatat | |
| 6,723,107 B1* | 4/2004 | Skiba et al. | 606/144 |
| 6,884,249 B2* | 4/2005 | May et al. | 606/148 |
| 2001/0041901 A1* | 11/2001 | Furusawa | 606/144 |
| 2002/0049458 A1 | 4/2002 | Singhatat | |
| 2002/0087178 A1 | 7/2002 | Nobles et al. | |
| 2003/0109891 A1* | 6/2003 | Dana et al. | 606/148 |
| 2004/0210238 A1* | 10/2004 | Nobles et al. | 606/114 |

OTHER PUBLICATIONS

Response Dated Dec. 15, 2010 to Requisition by the Examiner of Jul. 12, 2010 From the Canadian Intellectual Property Office Re. Application No. 2,557,732.

Supplementary European Search Report Dated Jun. 9, 2011 From the European Patent Office Re. Application No. 05709148.0.

Proceedings Further With the European Patent Application Pursuant to Rule 70(2) EPC Dated Jun. 28, 2011 From the European Patent Office Re. Application No. 05709148.0.

Requisition by the Examiner Dated Jul. 12, 2010 From the Canadian Intellectual Property Office Re. Application No. 2,557,732.

Response Dated Jul. 31, 2011 to Proceedings Further With the European Patent Application Pursuant to Rule 70(2) EPC of Jun. 28, 2011 From the European Patent Office Re. Application No. 05709148.0.

Response Dated Aug. 24, 2011 to Proceedings Further With the European Patent Application Pursuant to Rule 70(2) EPC of Jun. 28, 2011 From the European Patent Office Re. Application No. 05709148.0.

International Preliminary Report on Patentability Dated Sep. 14, 2006 From the International Bureau of WIPO Re.: Application No. PCT/IL2005/000254.

International Search Report and the Written Opinion Dated Feb. 6, 2006 From the International Searching Authority Re.: Application No. PCT/IL05/00254.

Requisition by the Examiner Dated Jul. 18, 2011 From the Canadian Intellectual Property Office Re. Application No. 2,557,732.

Communication Pursuant to Article 94(3) EPC Dated Dec. 1, 2011 From the European Patent Office Re. Application No. 05709148.0.

\* cited by examiner

SUTURE MANIPULATING AND CUTTING IMPLEMENT

RELATED APPLICATIONS

This application is a National Phase Application of PCT Patent Application No. PCT/IL2005/000254 having International Filing Date of Mar. 3, 2005, which claims the benefit of U.S. Provisional Patent Application No. 60/549,553 filed on Mar. 4, 2004. The contents of the above Applications are all incorporated herein by reference.

FIELD AND BACKGROUND OF THE INVENTION

The present invention relates to a suture manipulating implement, and particularly to a surgical instrument for manipulating a knotted suture to properly locate the knot thereof with respect to the tissue being sutured, and then for removing excess suture from the knot.

There is a growing demand to perform surgery, wherever possible, through small portals leading directly to the location operated on, thus minimizing damage to overlying and adjacent tissue. The technique is also known by the name endoscopy. Arthroscopy is the term used for the endoscopic approach applied to treat the various limb joints in the body.

As in all minimally invasive techniques, the area operated on is not exposed, and is not directly visible to the surgeon. The surgeon relies on a system of internal illumination and a small video camera. The camera projects an enlarged image onto a monitor screen to serve as a guide to the surgeon.

All necessary operations must be performed through a narrow opening. The size of this opening limits the size of the instruments used and the space available to manipulate them. In particular, access to tight joints is difficult. Small-size cutting, grasping, debriding and piercing instruments, capable of operating through small portals, have been developed for this purpose.

Suturing is also possible, and many suture passing and stitching devices are available to the arthroscopist. Tying a knot in situ is, however, barely possible.

The alternative solution is to use excess lengths of suture, and to bring the end of the strands to the outside for easy tying. One of several types of sliding knots, similar to the "hangman's knot", is formed at the outside and then, aided by one of several types of knot manipulating instruments, is moved down the remaining strand through the access portal and is tightened firmly over the tissue stitched. The excess length of suture is now cut off a small distance above the knot.

It will thus be seen that the features desirable for such an arthroscopic suture cutter include: small diameter, ease of use, clean cutting, controlled distance of cut from the knot, and capability of accommodating sutures of different diameters and materials. The length of the suture end remaining after cutting is important: If it is too long, it may cause irritation; if it is too short, the knot may fail to hold. Ideally, the instrument should be able to handle and cut all types and sizes of suture material in use.

Insofar as we are aware, all instruments available on the market fail to include one or more of the above desirable features. One such device, which has been on the market since 1999 and offers several advantages over others, consists of a pair of loop handles, an elongated tube, and a solid shaft mounted within the tube. A bore sized to allow a suture to be threaded through it is formed through the distal end of the shaft at an angle to its axis. The cross-section of this bore is in the form of a droplet, and the angle relative to the axis of the shaft causes the exit to be much elongated in shape. The distal end face of the shaft is countersunk to define a recess to accommodate the knot. The shaft slides freely within a tubular cutter member in the form of a hardened tube, the distal end of which is ground into a sharp cutting edge. Sliding the tube forwardly relative to the shaft forces a suture threaded through the bore, irrespective of its thickness, against the narrow, tapered portion of the bore exit for clean cutting. The tube is advanced until it cuts the suture at a length determined by the distance between the distal end of the shaft and the bore exit.

In use, the surgeon threads the free end of the suture strand into the bore of the shaft, and then holds the end of the suture to tension it, while advancing the instrument along the suture strand until the knot is reached. A spring loaded safety latch in the handle prevents accidental premature cutting. Releasing the latch allows the surgeon to operate the movable handle for cutting the suture strand.

One drawback of the above device is that it is difficult to thread the suture through the bore, especially under the conditions prevailing in the operating room. Many surgeons, therefore, prefer to use other devices, such as suture scissors, where the suture remains free, thus sacrificing important advantages for easier use. Also, the practicable dimensions of the bore restrict the range of suture types for which the device can be used.

Another known implement of this type is described in our U.S. patent application Ser. No. 10/323,795, filed Dec. 20, 2002, and assigned to the same assignee as the present application. That implement, however, also includes a bore through which the suture is to be threaded, and therefore would have the same drawbacks as described above with respect to the device commercially available since 1999.

OBJECT AND BRIEF SUMMARY OF THE PRESENT INVENTION

An object of the present invention is to provide a suture manipulating implement having advantages in one or more of the above respects.

According to one aspect of the present invention, there is provided an implement for manipulating a knotted suture during a surgical procedure, comprising: an elongated shaft having a proximal end engageable by the user for manipulating the instrument, and a distal end engageable with the knotted suture to be manipulated; the distal end of the elongated shaft having an end face formed with a recess for receiving the knot of the suture; characterized in that the distal end of the elongated shaft is formed with an open slot starting from a location spaced from the end face and extending along the outer surface of the elongated shaft to the recess in the end face, such as to enable the knotted suture to be introduced into the slot and the recess by effecting a sidewise movement of the knotted suture with respect to the elongated shaft, or vice-versa.

According to a further important feature in the preferred embodiment of the invention described below, the open slot is of a width to accommodate a wide range of suture sizes and materials.

According to still further features in the described preferred embodiment, the open slot is formed with a first section leading from the recess towards the proximal end of the elongated shaft, and a second section leading from a juncture with the first section towards the distal end of the elongated shaft but terminating short of the end face.

According to another aspect of the present invention, there is provided an implement for manipulating a knotted suture during a surgical procedure, and for removing an excess length of a suture, comprising: an elongated shaft having a proximal end engageable by the user for manipulating the implement, and a distal end engageable with the knotted suture to be manipulated; the distal end of the elongated shaft having an end face formed with a recess for receiving the knot of the suture; the distal end of the elongated shaft being further formed with an open slot starting from a location spaced from the end face and extending along the outer surface of the elongated shaft to the recess in the end face, such as to enable the knotted suture to be introduced into the slot and the recess by effecting a sidewise movement of the knotted suture with respect to the shaft member, or vice-versa; and a tubular cutter member enclosing the elongated shaft and effective to cut the suture in the slot upon movement of the elongated shaft with respect to the tubular cutter member, or vice-versa.

It will thus be seen that an implement constructed in accordance with the foregoing features enables the surgeon to introduce the suture into the open slot by a sidewise movement of the elongated shaft with respect to the knotted suture, or vice-versa. Such a movement can be much more conveniently executed by the surgeon, especially under the conditions prevailing in the operating room, than threading the suture through a bore in the implement as required by the prior devices. In addition, an implement using such an open slot for receiving the suture enables the implement to accommodate a much larger range of suture diameters, materials and types, than one using a bore for receiving the suture, and cuts the suture to a precise length above the knot.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF THE PRIOR ART
IMPLEMENT OF FIGS. 1-4

Figure 1:
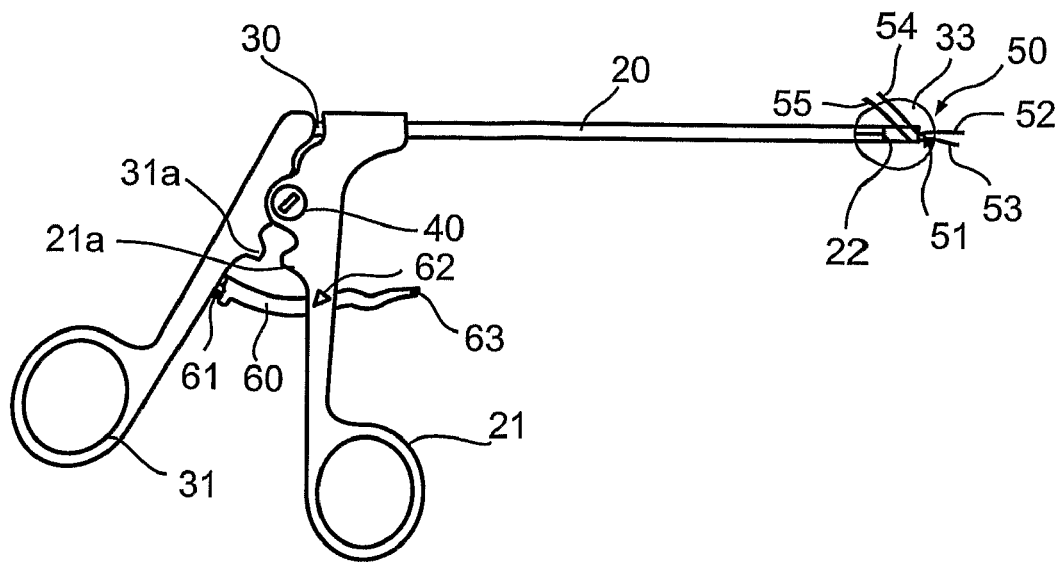
FIG. 1 illustrates a suture manipulating implement in accordance with the above-described prior art, and therefore subject to the drawbacks also described above.
Figure 2:
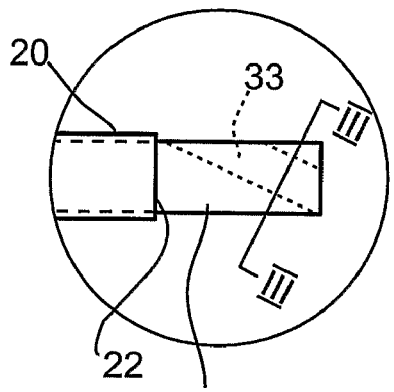
FIG. 2 is an enlarged fragmentary view of the distal end of the implement of FIG. 1.

FIG. 1 illustrates a suture manipulating and cutting implement constructed in accordance with the prior art as briefly described above. The illustrated implement includes a tubular cutter member 20 having a proximal end formed with a handle 21, and an elongated shaft 30 moveable within cutter member 20 and also having a proximal end formed with a handle 31. The two handles 21, 31 are pivotally mounted to each other about a pin 40.

The distal end of tubular cutter member 20 is formed with an annular cutter edge 22 on its inner surface circumscribing the outer surface of the elongated shaft 30.

Figure 3:
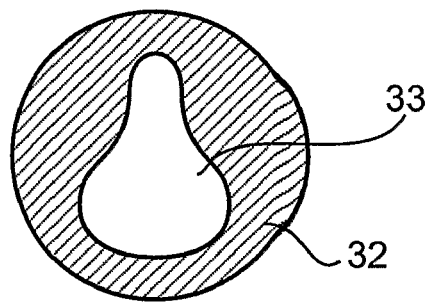
FIG. 3 is an enlarged sectional view of FIG. 2, along line III-III.
Figure 4:
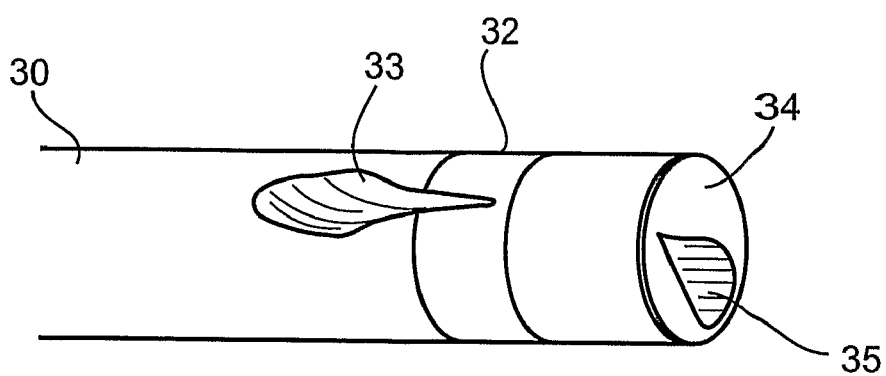
FIG. 4 is an enlarged three-dimensional view of the distal end of the prior art implement of FIG. 1.

Elongated shaft 30 has a distal end 32 formed with an angled bore 33 for receiving the suture, schematically shown at 50 in FIG. 1. Bore 33 is sized to allow suture 50 to be threaded through it at angle to the axis of shaft 30. The cross-section of bore 33 is in the form of a droplet as shown particularly in FIGS. 3 and 4. The end face 34 of elongated shaft 30 is countersunk to define a recess, as shown at 35 in FIG. 4, to accommodate the knot 51 of suture 50, with the ends of the suture 52, 53, extending through the angled bore 33.

The illustrated implement further includes a latch 60 secured at one end 61 to handle 31 and including a latching element 62 engageable with the other handle 21 so as to releasably retain the two handles in an initial spread-apart position, as shown in FIG. 1. Latch 60 includes a finger-piece 63 engageable by the user's finger to release latching element 62, and thereby to permit the two handles 21, 31, to be moved towards each other from the illustrated initial position, to an actuated position. During this movement the distal end 32 of the elongated shaft 30 is drawn into the distal end of the tubular cutter member 20 such that the annular cutter edge 22 of cutter member 20 engages and cuts-off the excess ends 51, 52 of the suture within angled bore 33.

The two handles 21, 31 are formed with stops 21a, 31a, which engage each other to limit the actuated position of the elongated shaft 30 with respect to the outer tubular member 20.

The manner of using the prior art implement illustrated in FIGS. 1-4 will be apparent from the above description. Thus, after the surgeon has applied the ends 52, 53 of the knotted suture 50 to the tissue being sutured and has formed the knot 51, the surgeon introduces the free ends 54, 55 of the two sutures through the angled bore 33, and seats the knot 51 into the recess 35 formed in the end face 34 of the distal end 33 of the elongated shaft 30. During this operation, the two handles 31, 32 of the implement are left in their spread-apart position, as shown in FIG. 1, to facilitate the manipulation of the knotted suture. When the excess ends of the knotted suture are to be removed, latch 60 is released by depressing finger-piece 63, thereby permitting the surgeon to move the two handles 31, 32 towards each other, and thereby draw the distal end 33 of elongated shaft 30 within the tubular cutter member 20, such that the annular cutter edge 22 of cutter member 20 engages and cuts-off the excess ends 54, 55 of the suture 50.

As described above, a serious drawback in this type of implement is the time and difficulty involved in threading the knotted suture through the angled bore 33, particularly during the conditions of a surgical operation. Another drawback is that the angled bore 33 can accommodate only a limited number of suture diameters and suture materials, thereby restricting the range of suture types for which the implement can be used.

DESCRIPTION OF PREFERRED EMBODIMENTS OF THE INVENTION

As briefly described above, the present invention provides a suture manipulating and cutting implement which does not suffer from the above-described drawbacks of the prior art implement illustrated in FIGS. 1-4. Briefly, this is done by providing the distal end of the elongated shaft formed with the recessed end face with an open slot, rather than with a bore, for receiving the knotted suture. Such a construction enables the knotted suture to be introduced into the slot and into the recess by effecting a sidewise movement of the shaft with respect to the knotted suture, or vice-versa. Moreover, such a construction enables a wide range of suture diameters and suture materials to be accommodated within the open slot, thereby enabling the suture to be used with a wide range of suture types.

Figure 5:
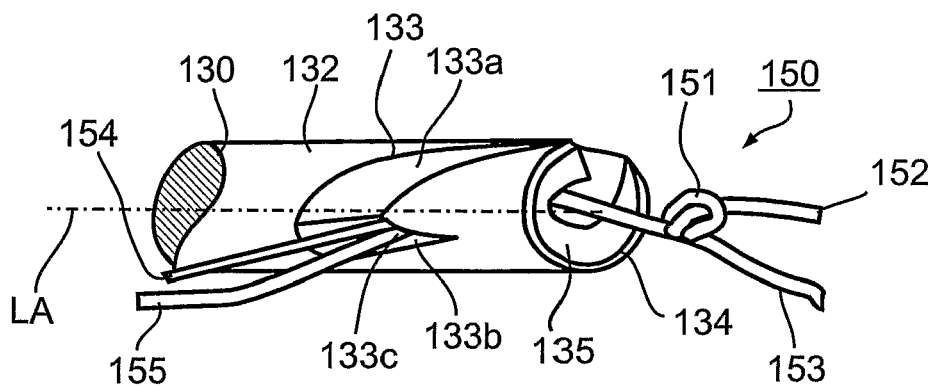
FIG. 5 illustrates the distal end of a suture manipulating and cutting implement constructed in accordance with the present invention, and having a knotted suture therein.
Figure 6:
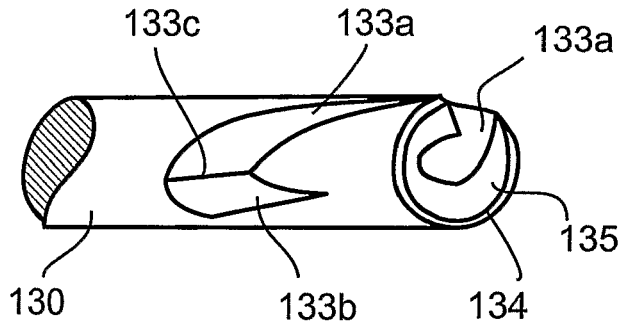
FIG. 6 illustrates the distal end of the implement of FIG. 5 but without the knotted suture.

The present invention, as illustrated in FIGS. 5 and 6, may be embodied in an implement of similar construction as the prior art device illustrated in FIGS. 1-4, by merely modifying the structure at the distal end 32 of the elongated shaft 30. Thus, FIGS. 5 and 6 illustrate only the elongated shaft, therein designated 130, its distal end 132, and the knotted suture 150 with which it coacts.

Thus, the distal end 132 of elongated shaft 130 also includes an end face 134 counter-sunk to define a recess 135 for receiving the knot 151 of the knotted suture 150. In this case, however, the distal end 132 of elongated shaft 130 is formed with an open slot 133 starting from a location spaced from the end face 134 and extending along the outer surface of the elongated shaft to recess 135 in the end face, such as to enable the knotted suture to be introduced into the slot and the recess by effecting a sidewise movement of the knotted suture with respect to the elongated shaft, or vice-versa. Slot 133 is of a width to accommodate a wide range of suture sizes and materials.

More particularly, slot 133 includes a first section 133a leading from recess 135 in end face 134 towards the proximal end of the elongated shaft 130, and a second section 133b leading from a juncture 133c with slot section 133a back towards the distal end of shaft 130 but terminating short of, but proximal to, its end face 134; the second section, 133b of the open slot 133 decreases in width from the juncture 133c to its end terminating short of, but proximal to, the end face of the shaft.

Slot section 133a is formed in a plane at an angle of 10-30 degrees, preferably 20 degrees, relative to the longitudinal axis LA of elongated shaft 130. Slot section 133b is formed in a plane parallel to the longitudinal axis LA of shaft 130 rotated 90 degrees with respect to the plane of slot section 133a. As seen in FIGS. 5 and 6, the width of each slot section 133a, 133b gradually decreases from the juncture 133c of the two sections towards the distal end of the elongated shaft. The inner surface of juncture 133c defines a bend for the suture, when received therein, and is rounded to permit sliding the suture within the slot without damaging the suture.

The manner of using the above-described implement, i.e., as illustrated in FIG. 1 but modified as described above with respect to FIGS. 5 and 6, will be apparent from the above description.

Thus, when using the implement during a surgical procedure, latch 60 would normally be in place, as shown in FIG. 1, to retain the two handles 21, 31 spaced apart, and the elongated shaft 130 in its initial position projecting outwardly of the tubular cutter member, as illustrated in FIG. 1. This is the fully open position of the implement, and is retained in this fully open position by latch element 62 engaging handle 21 as shown in FIG. 1. In this fully open position of the implement, the distal end 132 of elongated shaft 130 projects outwardly of the tubular cutter member (20, FIG. 1) so as to expose the complete open slot 133, including its two sections 133a and 133b, for loading the suture 150 into the slot. This can be conveniently done by effecting a sidewise movement of the implement with respect to the suture, to seat the suture within slot section 133a.

At this point, latch 60 (FIG. 1) is manually released to permit the two handles 21, 31 to be drawn towards each other to an intermediate position, such as to force the suture in slot section 133a to move into slot section 133b as shown in FIG. 5. Latch 60 may include a separate latching element (not shown in FIG. 1) engageable with handle 21 to releasably retain the two handles in this intermediate position. In this intermediate position, the distal end of the tubular cutter member formed with the annular cutter edge (22, FIG. 1) covers just the bend 133c of the open slot 133, thereby retaining the suture ends within slot section 133b. In this intermediate position of the two handles 21, 31, the surgeon, gripping the free ends 154, 155 of the knotted suture 150, is able to move the suture within slot section 133b and to seat the knot 151 within recess 135 in the end face of shaft 130.

The surgeon may then move the two handles 21, 31 to their fully closed positions, as determined by stops 21a, 31a (FIG. 1) of the two handles, whereupon the distal end 132 of the elongated shaft 130 is fully drawn into the tubular cutter (20, FIG. 1) such that its annular cutting edge (22, FIG. 1) cuts-off the excess ends 154, 155 of the two suture strands.

It will thus be seen that the novel construction, including the open slot 133, enables the surgeon to conveniently introduce the suture into the open slot by the above-described sidewise motion, which can be conveniently executed during an operation procedure. Moreover, the open slot construction inherently accommodates a wide range of suture dimensions, thereby enabling the implement to be used with different sizes and types of sutures. In addition, the length of the suture ends from the knot 151 will always be the same, namely the distance between the recess 135 in the end face 134 of shaft 130, and the distal end of slot section 133b.

Figure 7:
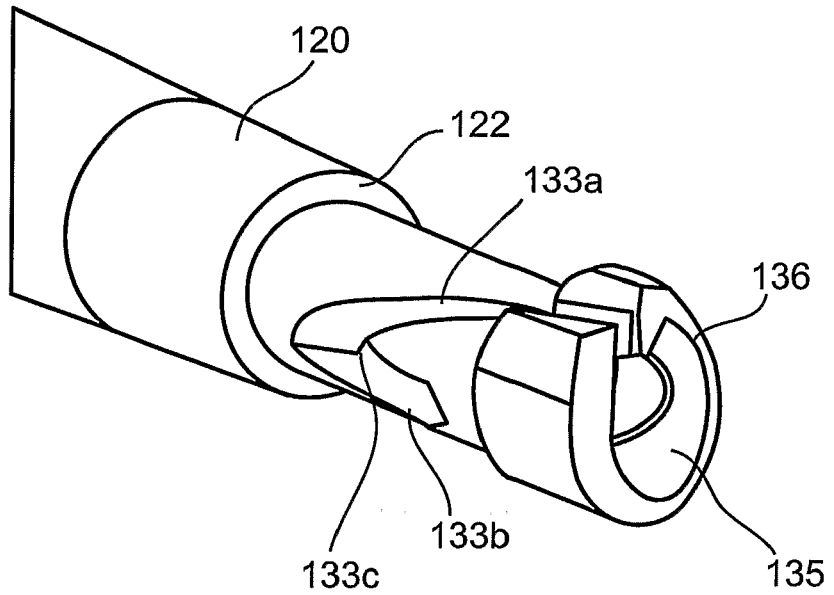
FIG. 7 illustrates a modification in the construction of the distal end of the implement of FIGS. 5 and 6.

FIG. 7 illustrates a modification in the construction of the distal end 133 of the elongated shaft 130. In this modification, the distal end formed with the recess 135 is of increased outer diameter, as shown at 136, to facilitate loading the suture into the slot. Thus, slot section 133a extends through the enlarged-diameter end 136 and provides a wider, chamfered opening of the slot to facilitate loading the suture while keeping the same basic width for the loaded suture. Thus, the suture will slide into the slot naturally when slot and suture are brought into alignment, thereby facilitating loading of the suture while working inside the body.

Another modification illustrated in FIG. 7 is that slot section 133b of the open slot 133 is of larger width than in FIGS. 5 and 6 so as to prevent the suture from becoming wedged within that slot section.

It will thus be seen that the implement illustrated in FIGS. 5-7 of the drawings permits convenient loading of a double-strand suture, manipulating the suture, and then cutting-off the excess ends. In addition, the implement is capable of accommodating a wide range of suture sizes, types, and materials of the suture, including double-strand sutures as shown.

In particular, the illustrated implement is capable of accommodating and cutting a double strand of the toughest suture material presently on the market to a precise length above the knot.

While the invention has been described with respect to two preferred embodiments, it will be appreciated that these are set forth merely for purposes of example, and that many other variations, modifications and applications of the invention may be made.

What is claimed is:

1. An implement for manipulating a knotted suture during a surgical procedure comprising: an elongate shaft having a proximal end engageable by the user for manipulating the instrument, and a distal end engageable with the knottable suture to be manipulated; said distal end of the elongated shaft having an end face formed with a countersunk opening for receiving the knot of the suture; wherein said distal end of the elongated shaft is formed with an open slot starting from the countersunk opening, such as to enable the knotted suture to be introduced into the open slot and the countersunk opening by effecting a sidewise movement of the knotted suture with respect to the elongated shaft, or vice versa; wherein the open slot is formed with a first section leading from said countersunk opening towards said proximal end of the elongate shaft, and a second section leading from a juncture with said first section back towards said distal end of the elongated shaft terminating short of the distal end and forming a V-shape; wherein said first slot section is formed in a plane at an angle of 10-30 degrees relative to the longitudinal axis of the elongate shaft; wherein said second slot section is formed in a plane parallel to the longitudinal axis of the elongated shaft.

2. The implement according to claim 1, wherein said open slot is formed of a width to accommodate a wide range of suture sizes and materials.

3. The implement according to claim 1, wherein the plane of said second slot section is rotated approximately 90 degrees with respect to the plane of said first slot section.

4. The implement according to claim 3, wherein the width of said first slot section also gradually decreases from said juncture toward said countersunk opening in the end face of the distal end of the elongated shaft.

5. The implement according to claim 4, wherein the inner surface of said slot engageable with a suture is rounded at said juncture of first and second slot sections.

6. The implement according to claim 1, wherein said distal end of the elongated shaft formed with said countersunk opening is of increased outer diameter, said open slot also extending through said distal end of increased outer diameter to said countersunk opening to facilitate loading the suture into said open slot.

7. The implement according to claim 1, wherein said implement
further comprises a tubular cutter member enclosing said elongated shaft and formed with an annular cutting edge engageable with a suture in the open slot of said elongated shaft upon movement of the elongated shaft with respect to the tubular cutter member, or by vice-versa.

8. The implement according to claim 7, wherein said implement further comprises a releasable latch for normally retaining said elongated shaft in an initial position wherein its distal end projects outwardly from the distal end of said tubular cutter member.

9. The implement according to claim 7, wherein the proximal end of the elongated shaft, and the proximal end of the cutter member, include handles pivotally mounted to each other to permit manipulating the implement and a suture received in said open slot of the elongated shaft, and actuating the implement to cause the cutter member to cut-off an excess length of the suture.

10. An implement for manipulating a knotted suture during a surgical procedure comprising: an elongate shaft having a proximal end engageable by the user for manipulating the instrument, and a distal end engageable with the knottable suture to be manipulated; said distal end of the elongated shaft having an end face formed with a countersunk opening for receiving the knot of the suture; wherein said distal end of the elongated shaft is formed with an open slot starting from the countersunk opening, such as to enable the knotted suture to be introduced into the open slot and the countersunk opening by effecting a sidewise movement of the knotted suture with respect to the elongated shaft, or vice versa; wherein the open slot is formed with a first section leading from said countersunk opening towards said proximal end of the elongate shaft, and a second section leading from a juncture with said first section back towards said distal end of the elongated shaft terminating short of the distal end and forming a V-shape; wherein said first slot section is formed in a plane at an angle of 10-30 degrees relative to the longitudinal axis of the elongate shaft; wherein said second slot section is formed in a plane parallel to the longitudinal axis of the elongated shaft; and a tubular cutter member enclosing said elongated shaft and effective to cut said suture in said open slot upon movement of the elongated shaft with respect to said tubular cutter member, or vice versa.

11. The implement according to claim 10, wherein the plane of said second slot section is rotated approximately 90 degrees with respect to the plane of said first slot section.

12. The implement according to claim 11, wherein said distal end of the elongated shaft formed with said recess is of increased outer diameter, said open slot also extending through said distal end of increased outer diameter to said recess to facilitate loading the suture into said open slot.

13. The implement according to claim 10, wherein said distal end of the elongated shaft formed with said recess is of increased outer diameter such as to define an annular finger-piece to facilitate introducing the suture into said slot, said open slot also extending through said annular finger-piece to said recess.

14. The implement according to claim 10, wherein said implement further comprises a releasable latch for normally retaining said elongated shaft in an initial position wherein its distal end projects outwardly from the distal end of said tubular cutter member.

* * * * *